United States Patent [19]
Beeuwkes, III

[11] Patent Number: 5,361,506
[45] Date of Patent: Nov. 8, 1994

[54] JAW OPENING MEASUREMENT DEVICE

[75] Inventor: Reinier Beeuwkes, III, Concord, Mass.

[73] Assignee: Therabite Corporation, Newtown Square, Pa.

[21] Appl. No.: 67,748

[22] Filed: May 26, 1993

Related U.S. Application Data

[63] Continuation of Ser. No. 810,023, Dec. 19, 1991, abandoned.

[51] Int. Cl.$^5$ .............. A61B 5/103; A61C 19/04; G01B 3/14; G01B 5/14
[52] U.S. Cl. ........................ 33/512; 33/514; 33/563; 128/777
[58] Field of Search .......... 33/512, 513, 514, 511, 33/562, 1 BB, 1 B, 1 D, 563; 128/777; D10/64, 62, 65, 70, 71

[56] References Cited

U.S. PATENT DOCUMENTS

| | | | |
|---|---|---|---|
| 1,649,664 | 11/1927 | Carter | 33/514 |
| 1,800,714 | 4/1931 | Clapp | 33/513 |
| 1,804,567 | 5/1931 | Pray | 33/513 |
| 2,154,148 | 4/1939 | Butts | 33/513 |
| 3,465,450 | 9/1969 | Hamilton | 33/511 |
| 4,352,663 | 10/1982 | Lee | 33/513 |
| 4,630,375 | 12/1986 | Spolyar | 33/512 |
| 5,158,096 | 10/1992 | Clark et al. | 128/777 |
| 5,226,428 | 7/1993 | Lee | 33/514 |

Primary Examiner—Christopher W. Fulton
Attorney, Agent, or Firm—James L. Jackson

[57] ABSTRACT

A measurement device is provided for measuring the degree of mandibular movement during therapy following maxillofacial surgery or to otherwise accomplish measurement of jaw movement. The measurement device is in the form of a flat object having a rounded end and defining a reference depression for receiving the incisal edge of the teeth of either the mandibular or maxillary arches. The measurement device includes a curved end and a slightly curved top which are provided with indicia to indicate the degree of jaw opening by comparing the location of an incisal edge with respect to the indicia. The measurement device along a straight end is provided with measurement indicia to enable effective measurement of lateral jaw movement and to accomplish measurement of movement relative to the occlusal plane of the patient's dentition.

6 Claims, 1 Drawing Sheet

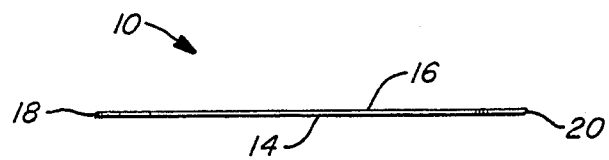
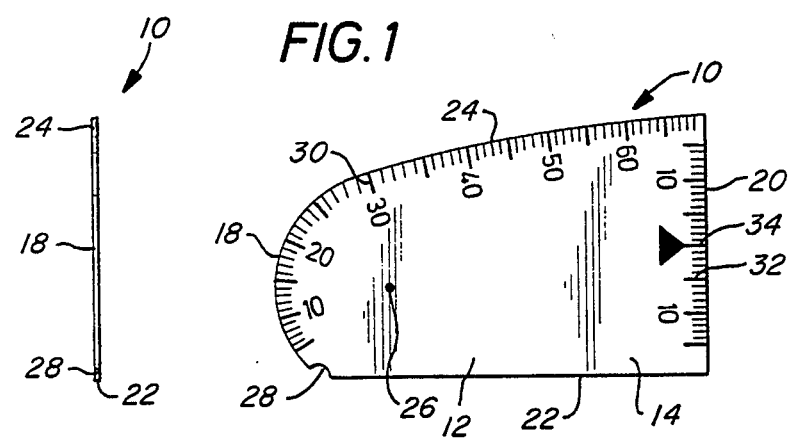
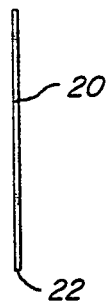
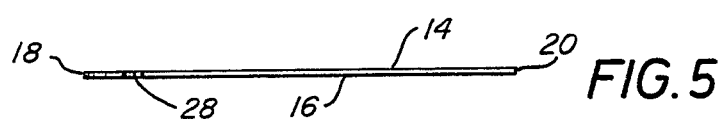
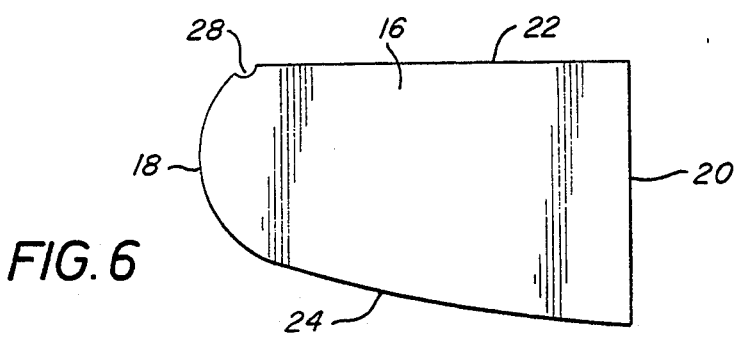

5,361,506

JAW OPENING MEASUREMENT DEVICE

This is a continuation-in-part of the subject matter of U.S. application Ser. No. 07/810,023, filed Dec. 19, 1991, by Reinier Beeuwkes, III and entitled Jaw Opening Measurement Device, now abandoned.

FIELD OF THE INVENTION

This invention relates generally to apparatus for use in connection with maxillofacial surgery and more particularly concerns a measurement device for use during therapy following maxillofacial surgery for accurately measuring the degree of jaw opening of a patient undergoing therapy to thus provide medical personnel with the capability of accurately determining the results of therapy and the progress of the patient toward recovery.

BACKGROUND OF THE INVENTION

Exercise of jaw muscles is an important part of treatment and rehabilitation for many jaw injuries and disorders. For example, the common practice of wiring jaws closed as a splinting approach to fractures and bone surgical procedures leads to a shortening of the muscles that close the jaw and a weakening of the muscles that open it. As a result, patients may find it impossible to open their mouths after the wiring has been removed. Physicians and surgeons resort to expedients which include prying with tongue depressors and the use of screw operated wedge devices to stretch the muscles and thereby accomplish opening of the mouth. Once the jaws are opened, it is necessary for patients to undertake exercises to stretch the muscles in order to regain full freedom of motion. Though to date jaw exercise devices have considered only opening and closing movement of the jaw, it may be desirable to impart lateral as well as pivotal movement to the mandible during its normal opening and closing movement as therapeutic movement of the temporo-mandibular joint as well as the muscle system for mandibular control. Passive elastic devices have been suggested for accomplishing jaw exercising. Also, expensive spring operated instruments have been developed for this purpose.

A typical defect of most commercially available jaw exercising devices is that they either cause pain and injury through exertion of excessive force or they may apply pressure to the molar region in a vertical manner thus displacing the condyles downward and disrupting the temporo-mandibular joint. None of these devices moves the lower jaw in a fashion which takes into account the structural features of the jaw hinge established by the temporo-mandibular joint, namely that the pivotal area of the jaw hinge is above and to the rear of the mouth opening by virtue of the curvature of the jaw at its upper rear portion and that the temporo-mandibular joint does not establish a single precise, pivot point about which the mandible rotates. Rather, the temporo-mandibular joint forms a movable pivot which causes compound movement of the mandible throughout its rotation.

During the healing period following maxillofacial surgery, as mentioned above, the mandible is typically immobilized by wires or other suitable retainers to stabilize the bone structure during its healing. After an appropriate period of healing has been accomplished the mandible is released from its stabilized relation with respect to the maxillary arch and a period of therapy begins. During therapy, as the jaw muscles return from their typically atrophied condition and as the temporo-mandibular joint recovers from its lack of vertical and lateral movement, it is desirable to measure the degree of jaw opening and lateral jaw movement that can occur as the patient's therapy progresses. It is desirable therefore to provide a measurement device having the capability of measuring vertical jaw movement from a particular reference and also having the capability of measuring lateral jaw movement in relation to a particular reference.

Because a jaw movement measuring device may come into contact with oral fluid it is particularly desirable to provide a measurement device that can be autoclaved or otherwise rendered sterile or which can be disposed of in order to prevent any cross contamination that might otherwise occur between patients or between the medical personnel and a patient. It is thus desirable to provide a jaw opening and lateral movement measuring device which is effective for selective measurement of both jaw movement and lateral jaw movement and which can also be sterilized or disposed of as desired by the user to prevent the possibility of bacterial or viral cross contamination.

SUMMARY OF THE INVENTION

It is a principle feature of the present invention to provide a novel jaw opening measurement device which may be simply and efficiently utilized by medical personnel to identify the degree of jaw opening that has been accomplished by therapy following maxillofacial surgery or other similar procedures that require immobilization of the jaw for a period of healing.

It is another feature of this invention to provide a novel jaw opening measurement device which is of simple nature and can be produced at low cost and yet provides for effective measurement of the jaw opening and lateral jaw movement of a patient.

It is an even further feature of this invention to provide a novel jaw measurement device which is of sufficiently small size, can be efficiently carried on the person or in clothing pockets of medical personnel so as to be readily available for use.

It is also a feature of this invention to provide a novel jaw measurement device which is of sufficiently low cost nature as to be readily disposable so as to minimize the possibility of cross contamination between patients.

Briefly, the various objects and features of the present invention are accomplished through the provision of a measurement device which is used by medical personnel or by the patient or those in attendance with the patient for selectively measuring jaw opening and lateral jaw movement in relation to specific references. The measurement device is typically in the form of a substantially flat plate composed of metal, polymer, cardboard or any other suitable material. The measurement device defines a reference depression adjacent one end thereof which is adapted to receive the incisal edge of a patient's mandibular or maxillary dentition. Adjacent the reference depression the measurement device defines a curved extremity provided with indicia which may be aligned with the incisal edge of the opposite mandibular or maxillary dentition for specific measurement of the degree of jaw opening that the patient can accomplish at any stage during therapy. The measurement device also includes a gradually curved upper edge portion which is smoothly merged with the curved extremity and which is also provided with indicia to provide for identification of the patient's jaw opening capability.

At the end of the measurement device opposite the curved extremity there is defined a straight edge portion which is also provided with indicia. This indicia incorporates a substantially centrally located reference line which may be aligned with an interproximal space such as between central incisors of the patient and which identify the degree of lateral jaw movement in either direction relative to the central reference line.

The indicia and perhaps other printed matter such as advertising for example, may be printed on the measurement device such as by silk screening, offset printing or by any other suitable process. Further, the indicia may be molded into the article during the manufacturing process if so desired.

BRIEF DESCRIPTION OF THE DRAWINGS

So that the manner in which the above recited features, advantages and objects of the present invention are attained and can be understood in detail, a more particular description of the invention, briefly summarized above, may be had by reference to the embodiments thereof which are illustrated in the appended drawings.

It is to be noted, however, that the appended drawings illustrate only typical embodiments of this invention and are therefore not to be considered limiting of its scope, for the invention may admit to other equally effective embodiments.

In the Drawings

FIG. 1 is an elevational view of a jaw measurement device constructed in accordance with the principles of the present invention;

FIG. 2 is a plan view of the jaw measurement device of FIG. 1;

FIG. 3 is a side elevational view of the jaw measurement apparatus of FIG. 1;

FIG. 4 is a fight side elevational view of the jaw measurement apparatus of FIG. 1;

FIG. 5 is a bottom view of the jaw measurement apparatus of FIG. 1; and

FIG. 6 is a rear view of the jaw measurement apparatus of FIG. 1.

DETAILED DESCRIPTION OF PREFERRED EMBODIMENT

Referring now to the drawings and first to FIG. 1 a jaw measurement device constructed in accordance with the present invention is illustrated generally at 10 and is generally in the form of a substantially flat sheet 12 having a flat front surface 14 and a flat rear surface 16. Surfaces 14 and 16 are preferably parallel, but may be of other suitable configuration as suits the needs of the user.

As shown in FIGS. 1 and 3 one end 18 of the measurement device 10 is of curved configuration while the opposite end 20 is straight and is oriented in substantially 90° relation with a straight bottom edge 22. The top edge 24 of the measurement device 10 is gradually curved and merges smoothly with the rounded end 18. The rounded end 18 is of generally arcuate configuration being formed about a point 26.

Near the bottom and adjacent one end of the measurement device there is defined a small depression 28 which is adapted to receive the inside edge of mandibular teeth of a patient when a jaw opening measurement is being accomplished. The depression 28 therefore establishes a measurement reference for that particular patient.

At the top and about the curved end 18 of the measurement device there is provided indicia which is marked to identify the degree of jaw opening with reference to the referenced depression 28. Thus, when the mandibular dentition is in engagement with the referenced depression 28 the incisal edges of the maxillary dentition will provide an indication of the degree of jaw opening that has been accomplished. Similar indicia 32 is provided along the straight extremity 20 and thus provides another form of measurement which can be utilized by medical personnel for identifying the degree of jaw opening that has been accomplished and for accomplishing other measurements that are appropriate to therapy following maxilla-facial surgery. The indicia 32 is effective for measuring lateral mandible movement relative to the maxilla. To accomplish this the central line 34 can be aligned with an interproximal space such as the interproximal space between the central incisors. The jaw may be moved by the patient to the extent of the patient's capability at this particular point in the therapy. The precise extent of lateral jaw movement can thus be measured and recorded. By comparing the patient's capability of increased lateral jaw movement as therapy continues medical personnel will be able to determine the patient's progress. Medical personnel will also be capable of determining the extent of movement of the temporal mandibular joint and to thus determine if the therapy is proper not only for accomplishing jaw opening movement but also to accomplish lateral jaw movement and movement of the temporomandibular joint. The indicia 32 defines a central measurement line 34 to thus enable medical personnel to achieve measurement from a centrally located reference such as the occlusal plane of the patient's dentition.

The measurement device 10 may be manufactured of many different types of suitable material. For example, it may be molded from any one of a number of suitable polymer materials such as polypropylene, polystyrene, etc. If so manufactured, the indicia may be printed onto the device 10 by a silk screen process or by any other suitable printing process. Further, the indicia may be molded into the article as the article is manufactured. The measurement device may also be manufactured of a paper product such as cardboard which may be coated by means of a polymer or by any other suitable means to prevent oral fluids from contaminating the material of the measurement device. If desired, the measurement device may also be composed of metal or any other suitable material that may be autoclaved or otherwise rendered to a sterilized condition for repeated use. Since certain changes or modifications may be made in the disclosed embodiment without departing from the inventive concepts involved, it is the aim of the appended claims to cover all such changes and modifications falling within the true spirit and scope of the present invention.

What is claimed is:

1. A measurement device for measuring the degree of jaw opening and lateral jaw movement of a human subject, comprising:

(a) a measurement body defining a reference depression adjacent one end thereof and having a curved edge said measurement body defining a straight edge at the end thereof opposite said curved edge;

(b) first indicia being present on said measurement body about said curved edge and relating to said reference depression; and (c) second indicia being provided along said straight edge and defining a reference line from which lateral jaw movement is determined, said reference line being substantially centrally located in reference to said straight edge.

2. The measurement device of claim 1, including:

(a) a curved upper portion merging smoothly with said curved edge; and (b) said first indicia also extending along said curved upper portion in reference to said reference depression.

3. The measurement device of claim 2, including:

said curved upper portion defining the upper edge of said measurement device.

4. The measurement device of claim 1, including:

said curved edge defining one extremity of said measurement device.

5. A measurement device for measuring the degree of jaw opening and lateral jaw movement of a human subject, comprising:

(a) a measurement body defining a reference depression adjacent one end thereof and having a curved edge and defining an upper edge; and (b) first indicia being present on said measurement body about said curved edge and relating to said reference depression, said first indicia also extending along said upper edge of said measurement body;

(c) said measurement body further defining a substantially straight edge at the end thereof opposite said curved edge; and (d) second indicia being provided along said substantially straight edge and defining a reference line from which lateral jaw movement is measured, said reference line being substantially centrally located in reference to said straight edge.

6. The measurement device of claim 5, including:

said upper edge of said measurement device being of curved configuration.

* * * * *